United States Patent
Addis (10) Patent No.: US 6,171,328 B1
(45) Date of Patent: Jan. 9, 2001

(54) INTRAVASCULAR CATHETER FILTER WITH INTERLOCKING PETAL DESIGN AND METHODS OF USE

(75) Inventor: Bruce Addis, Redwood City, CA (US)

(73) Assignee: Embol-X, Inc., Mountain View, CA (US)

( * ) Notice: Under 35 U.S.C. 154(b), the term of this patent shall be extended for 0 days.

(21) Appl. No.: 09/437,097

(22) Filed: Nov. 9, 1999

(51) Int. Cl.⁷ .................................................. A61M 29/00
(52) U.S. Cl. ............................................................ 606/200
(58) Field of Search ..................................... 606/200, 159, 606/191, 195, 127, 128

(56) References Cited

U.S. PATENT DOCUMENTS 5,707,359 * 1/1998 Bufalini ................................ 606/200
5,827,324 * 10/1998 Cassell et al. ........................ 606/200

* cited by examiner

Primary Examiner—Michael Buiz
Assistant Examiner—Kevin Truong
(74) Attorney, Agent, or Firm—Lyon & Lyon LLP (57) ABSTRACT

A filter device for temporary placement of a filter in an artery or vein is disclosed. The device includes an expandable filter mounted on a distal end of a catheter. The filter comprises a plurality of circumferentially adjacent porous segments which are arranged generally about the surface of a cone having an open base, and the segments are engaged to one another by means, such as a hook. The filter conforms to the interior of a vessel wall when expanded and contracts to a consistent diameter without bunching when stowed. Methods of using the filter device to entrap and remove embolic material from a vessel during endovascular procedures are also disclosed.

20 Claims, 5 Drawing Sheets

INTRAVASCULAR CATHETER FILTER WITH INTERLOCKING PETAL DESIGN AND METHODS OF USE

FIELD OF THE INVENTION

The present invention relates generally to devices and methods for providing temporary placement of a filter in a blood vessel. More particularly, the invention provides a filter structure that conforms to the interior vessel wall with minimum gap and can be stowed to facilitate its passage across large vascular lesions.

BACKGROUND OF THE INVENTION

Treatment of thrombotic or atherosclerotic lesions in blood vessels using an endovascular approach has recently proven to be an effective and reliable alternative to surgical intervention in selected patients. For example, directional atherectomy and percutaneous translumenal coronary angioplasty (PTCA) with or without stent deployment are useful in treating patients with coronary occlusion. Atherectomy physically removes plaque by cutting, pulverizing, or shaving in atherosclerotic arteries using a catheter-deliverable endarterectomy device. Angioplasty enlarges the lumenal diameter of a stenotic vessel by exerting mechanical force on the vascular walls. In addition to using angioplasty, stenting, and/or atherectomy on the coronary vasculature, these endovascular techniques have also proven useful in treating other vascular lesions in, for example, carotid artery stenosis, peripheral arterial occlusive disease (especially the aorta, the iliac artery, and the femoral artery), renal artery stenosis caused by atherosclerosis or fibromuscular disease, superior vena cava syndrome, and occlusive iliac vein thrombosis resistant to thrombolysis.

It is well recognized that one of the complications associated with endovascular techniques is the dislodgment of embolic materials generated during manipulation of the vessel, thereby causing occlusion of the narrower vessels downstream and ischemia or infarct of the organ which the vessel supplies. In 1995, Waksman et al. disclosed that distal embolization is common after directional atherectomy in coronary arteries and saphenous vein grafts. See Waksman et al., American Heart Journal 129(3): 430-5 (1995), incorporated herein by reference. This study found that distal embolization occurs in 28% (31 out of 111) of the patients undergoing atherectomy. In January 1999, Jordan, Jr. et al. disclosed that treatment of carotid stenosis using percutaneous angioplasty with stenting is associated with more than eight times the rate of microemboli seen using carotid endarterectomy. See Jordan, Jr. et al. Cardiovascular surgery 7(1): 33-8 (1999), incorporated herein by reference. Microemboli, as detected by transcranial Doppler monitoring in this study, have been shown to be a potential cause of stroke. The embolic materials include calcium, intimal debris, atheromatous plaque, thrombi, and/or air.

There are a number of devices designed to provide blood filtering for entrapment of vascular emboli. Ginsburg, U.S. Pat. No. 4,873,978, discloses an arterial filtering system, which includes a catheter with a strainer device at its distal end. This device is inserted into the vessel downstream from the treatment site and, after treatment, the strainer is collapsed around the entrapped emboli and removed from the body. The Ginsburg device could not withstand flow rates of 5 L/min. It is designed for only small arteries and therefore could not capture emboli destined for all parts of the body. Ing. Walter Hengst GmbH & Co, German Patent DE 34 17 738, also discloses another arterial filter having a folding linkage system which converts the filter from the collapsed to the expanded state.

Another method for removing embolic debris is using an endovascular aspiration catheter. The method requires placement of an occlusion device distal to the region of interest to provide protection against distal embolization while embolic debris are aspirated by the catheter. The major disadvantage associated with the aspiration catheter is that blood flow distal to the occlusion is compromised during total occlusion of the vessel, which may result in tissue ischemia or death.

Filters mounted to the distal end of guidewires have been proposed for intravascular blood filtration. A majority of these devices includes a filter which is attached to a guidewire and is mechanically actuated via struts or a pre-shaped basket which deploys in the vessel. These filters are typically mesh "parachutes" which are attached to the shaft of the wire at the distal end and to wire struts which extend outward in a radial direction at their proximal end. The radial struts open the proximal end of the filter to the wall of the vessel. Blood flowing through the vessel is forced through the mesh thereby capturing embolic material in the filter. These devices are self-directing and can be placed intravascularly. However, there are several disadvantages associated with guidewire-filtration. First, the steerability of the guidewire may be altered as compared to conventional guidewires due to the size of the filter, and the guidewire may bend, kink, and/or loop around in the vessel, making insertion of the filter through a complex vascular lesion difficult. Secondly, the current filter designs, e.g., a basket or net, often fail to conform to the internal perimeter of the vessel, and distal embolization can still occur despite the filter placement. Thirdly, as the filter is stowed, the filter material is gathered together with "bunching" of the material at the perimeter, causing uncontrolled gathering and creating relatively large and poorly defined crossing profiles. As a result, the current filter designs require large capture sheaths to deploy and stow the filter.

Moreover, there are several problems associated with the current construction of the filter material. For example, the present method for creating a mesh, weave, or membrane having a specified pore opening to trap debris relies on the thread size used in the weave. When deployed in a vessel, the weave creates flow dynamics that activate the clotting mechanism, leading to thrombi formation. The filter material is also injurious to the red blood cells as they traverse the filter, causing intravascular hemolysis.

What is needed are simple and safe blood filtering devices that conform to a patient's vessel wall to prevent distal embolization during endovascular procedures, and provide easy steerability and a uniform controlled closure profile when stowed. Existing devices are inadequate for this purpose.

SUMMARY OF THE INVENTION

The present invention provides devices and methods which protect a patient from distal embolization during cardiovascular procedures, e.g., atherectomy, angioplasty, or stent-deployment. More specifically, filter devices that require small sheaths for deployment and conform to the interior vessel wall with minimum gap are disclosed for capturing embolic material generated during a procedure in an artery or vein.

In one embodiment, the filter device comprises a catheter and an expandable filter mounted at a distal end of the catheter. The filter has a plurality of circumferentially adjacent porous segments, arranged like the petals of a flower. Each petal is constructed from a biocompatible material, such as plastic (e.g., polyester (mylar), polyethylene tetrachloride, polyethylene, or polyvinylidene fluoride (kynar)) or metal (e.g., stainless steel, nitinol, platinum alloy, or molybdenum alloy). The processing used to create pores in the petals could be either laser or chemical etching, stamping, or cutting by hand. The pores are precision machined into the filter material, thereby providing less traumatic pathways for blood flow and minimizing activation of the intravascular clotting process. Each petal is shaped generally as an equilateral triangle having two sides and a base. Each side has means, e.g., a hook, to engage the adjacent petals. The petals are arranged generally about the surface of a cone. In certain embodiments each petal has an extension bonded to the center of the arc and extending away from the arc. Each extension is bonded to the catheter. The filter opens by expanding an open base of the cone until the means for engaging the adjacent petals interlocks, preventing further expansion. In other embodiments, expansion of the petals is limited by a capture sleeve. The capture sleeve can engage the vertex of the conical structure formed by the petals, and this engagement will limit further expansion of the petals. Thus, in this embodiment, interlocking edges are not necessary.

In another embodiment, each porous petal has the shape of a sector bounded by two radii and the included arc of a circle. The base of the cone opens proximal a vertex of the cone, and the catheter extends distally beyond the vertex of the cone. In other devices this orientation is reversed, i.e., the base of the cone opens distal the vertex of the cone. In certain embodiments, the catheter includes an atraumatic tip at the distal end.

In another embodiment, the catheter includes an additional closure mechanism, such as a plurality of struts attached to the vertices of the petals to provide proximal stowage. In certain embodiments, the distal end of the catheter includes a capture sheath which comprises a tubular member having a lumen shaped to receive the conical filter for additional filter protection when the filter is stowed. The small size of the capture sheath allows easy passage of the filter through a tight stenotic lesion.

In other embodiment, the capture sheath is constructed of a porous material capable of filtering blood. In use, the porous petals are expanded to the shape of a cone, and the petals collect embolic debris as blood flows through the pores. The petals are then contracted and stowed within the capture sheath. Blood continues to flow against the petals within the capture sheath, thereby washing the debris from the petals. The embolic debris then collects within the porous capture sheath.

In another embodiment, the petals are impermeable to blood. Rather than filtering blood, the petals act as a funnel channeling blood and emboli through an opening disposed at the vertex of the cone. The blood then passes through a capture sheath constructed of porous material capable of acting as a filter. The capture sheath may be formed of any of the materials discussed herein as suitable for the interlocking petals. Thus, blood flows into the funnel, through the central opening, and through the capture sheath, wherein emboli are filtered and retained by the capture sheath.

In another embodiment, the catheter includes an angioplasty balloon at a distal region. In certain embodiments, a stent is included in the distal region and is expanded by the angioplasty balloon. In other embodiment, a self-expanding stent, which is constructed from a shape-memory material, e.g., nitinol, is mounted at the distal region.

The filter devices of the present invention are most useful in capturing embolic debris generated during endovascular procedures within a coronary artery, aorta, common carotid artery, external and internal carotid arteries, brachiocephalic trunk, middle cerebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery, and all other arteries carrying oxygenated blood. The filter devices are also useful in preventing distal embolization in the venous circulation, including the superior vena cava, inferior vena cava, external and internal jugular veins, brachiocephalic vein, pulmonary artery, subclavian vein, brachial vein, axillary vein, iliac vein, renal vein, femoral vein, profunda femoris vein, great saphenous vein, portal vein, splenic vein, hepatic vein, and azygous vein.

In a first method of using the filter device, the filter is placed in a contracted state. The distal end of the catheter is inserted percutaneously through an artery or vein and advanced into or beyond a region of interest, typically a stenotic lesion caused by buildup of atherosclerotic plaque and/or thrombi. The filter is then expanded downstream of the vascular occlusion by expanding the open base until locking of the interlocking adjacent petals. In this way, the bases of the porous petals conform to the interior vessel wall with minimum gap. After the stenotic lesion is removed by endovascular procedure(s), e.g., angioplasty or atherectomy, the filter is collapsed and removed from the vessel, together with the captured embolic debris. When the filter is stowed, the petals slide over one another, creating a consistent diameter when constricted by a sheath. In this way, bunching of the filter and dislodgment of the captured embolic debris are avoided.

It will be understood that there are several advantages to using the filter devices and methods disclosed herein for capturing and removing embolic debris during endovascular procedures. For example, the filter device (1) is particularly well suited for temporary filtration of blood in any vessel to entrap embolic debris, thereby minimizing neurologic, cognitive, and cardiac complications associated with distal embolization, (2) conforms to the interior vessel wall with minimum gap, (3) includes pores which minimize injury to the red cells and activation of the intravascular coagulation pathways, (4) can be stowed to a uniform and predictable size, (5) can be delivered over a guidewire as a rapid exchange device, (6) includes an atraumatic distal tip to minimize vessel wall injury, (7) may include a distal filter/capture tube for additional filter protection and containment of embolic debris during towage, (8) enables an operator to steer and deploy the filter without kinking, bending, and/or looping of the catheter because of the small size ratio of filter to catheter, and (9) can be used in adult and pediatric patients.

DETAILED DESCRIPTION

Figures 1A, 1B, 1C, 2:
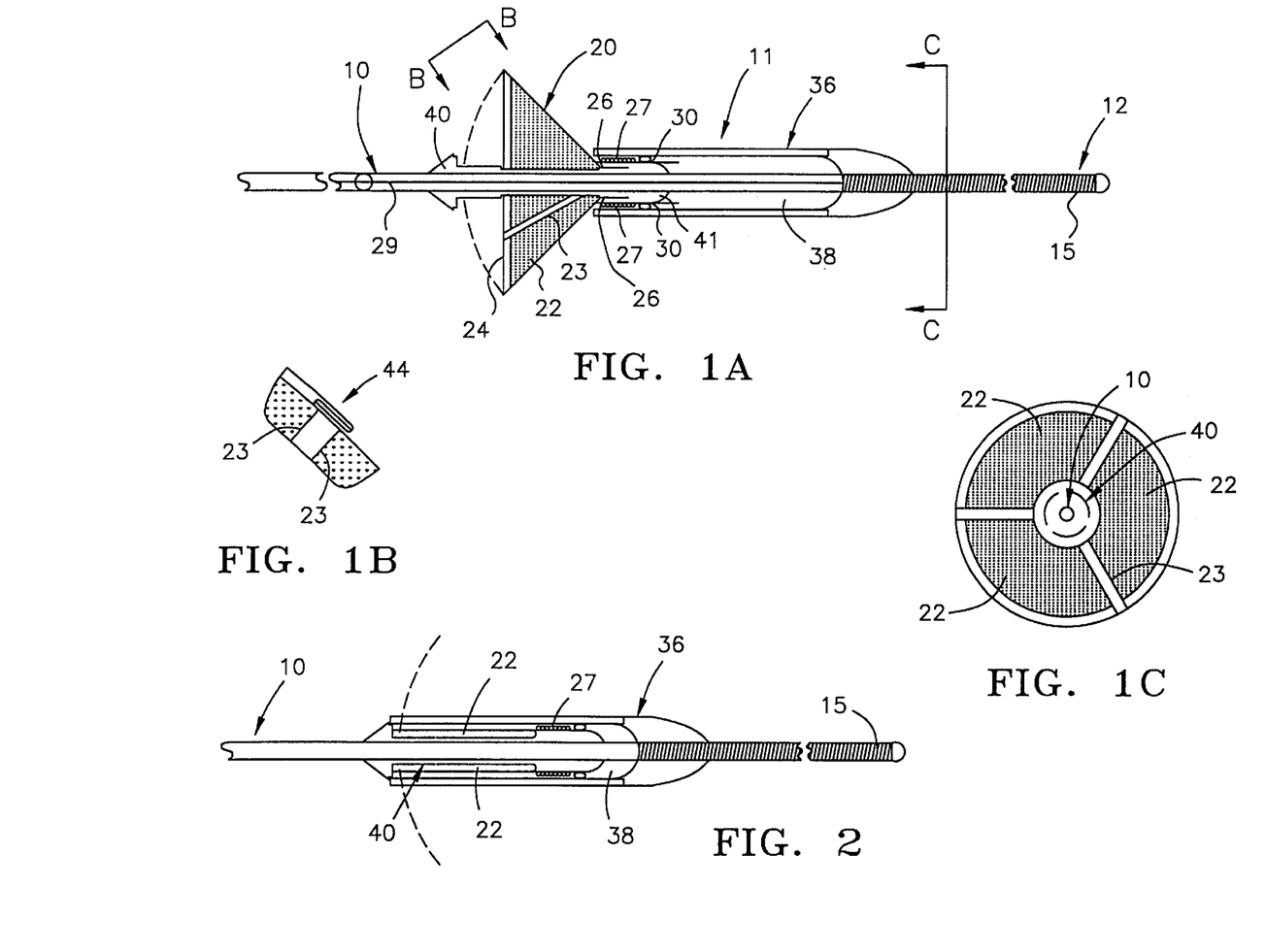
FIG. 1A depicts an embodiment of the catheter filter device in an expanded condition according to the present invention.
FIG. 1B depicts a view of the filter through section line B—B and which shows the interlocking mechanism which engages circumferentially adjacent petals.
FIG. 1C depicts a distal view of the filter from section line C—C of the catheter filter device having sector-shaped petals.
FIG. 2 depicts the embodiment of the catheter filter device of FIG. 1A in a collapsed condition.

A catheter filter device for temporary placement in a vessel, either an artery or vein, is provided as depicted in FIGS. 1A, 1B, and 1C. Catheter 10 has a proximal end, distal region 11, and distal end 12. Atraumatic floppy tip 15, mounted at distal end 12, facilitates insertion of the filter in a vessel and minimizes injury to the vascular wall. Expandable filter 20, which is mounted on distal region 11, may comprise 2, 3, 4, 5, 6, 7, 8, 9, 10, 11, 12, or any other suitable number of circumferentially adjacent porous petals.

In FIGS. 1A and 1C, filter 20 comprises three triangular petals 22 which are bounded by sides 23 and base 24. Each petal has pores that are precision machined by laser, etching, and/or chemical milling to provide less traumatic pathways for blood flow. Anticoagulants, such as heparin and heparinoids, may be applied to the petals to reduce thrombi formation. Bases 24 of petals 22 are arranged about the base of an open cone, i.e., the perimeter of the expanded filter, which makes contact with a vessel wall with minimum gap.

Each petal 22 also includes extension 26 that is bonded to the vertex of the triangle and extends away from base 24. Each extension is also bonded to distal end 41 of actuating mechanism 40 by wires 27 wrapped about each extension. The filter is expanded or contracted by operating actuating mechanism 29 from the proximal end of catheter 10. Extensions 26 also include radiopaque markers 30, which provide information on the position of filter 20 under fluoroscopy. Capture sheath 36, which is included in distal region 11 of catheter 10 and bonded to actuating mechanism 29, facilitates stowage of filter 20. Sheath 36 comprises a tubular member having lumen 38 for receiving filter 20 when the filter is contracted by moving actuating mechanism 29 proximally.

Edges 23 of each triangular petal 22 include means that engages the circumferentially adjacent petals. In FIG. 1B, adjacent petals 22 are engaged by hook 44, shown here as interlocking folds along the edge of each side. Filter 20 opens by expanding the open base until hooks 44 engage adjacent petals, preventing further expansion.

In certain embodiments, the base of each petal 22 is curved, such that each petal has the shape of a sector bounded by two radii and the included arc of a circle. FIG. 1C depicts a distal view of filter 20 having three petals, each of which has the shape of a sector having radii 23 and an arc of approximately 10–120°, more preferably approximately 30–110°, more preferably approximately 50–100°, more preferably approximately 70–90°, and most preferably approximately 84.9°.

In certain embodiments, capture sheath 36 is constructed of a porous material capable of filtering blood. In use, porous petals 22 are expanded to the shape of a cone, and the petals collect embolic debris as blood flows through the pores. The petals are then contracted and stowed within capture sheath 36 as shown in FIG. 2. Blood continues to flow against petals 22 within capture sheath 36, thereby washing the debris from the petals. The embolic debris then collects within porous capture sheath 36.

In other embodiments, petals 22 are impermeable to blood. Rather than filtering blood, the petals act as a funnel channeling blood and emboli through an opening disposed at the vertex of the cone. Blood then passes through sheath 36 constructed of porous material capable of acting as a filter. Sheath 36 may be formed of a biocompatible material, such as plastic (e.g., polyester (mylar), polyethylene tetrachloride, polyethylene, or polyvinylidene fluoride (kynar)) or metal (e.g., stainless steel, nitinol, platinum alloy, or molybdenum alloy). Thus, blood flows into the funnel, through the central opening, and through sheath 36, wherein emboli are filtered and retained by the capture sheath.

To place the filter of FIG. 1A in a collapsed condition as depicted in FIG. 2, actuating mechanism 29 is operable from the proximal end of catheter 10 to withdraw lumen 38 of capture sheath 36 over petals 22. Petals 22 slide over one another when being stowed, thereby creating a consistent diameter when constricted by sheath 36.

Figure 3:
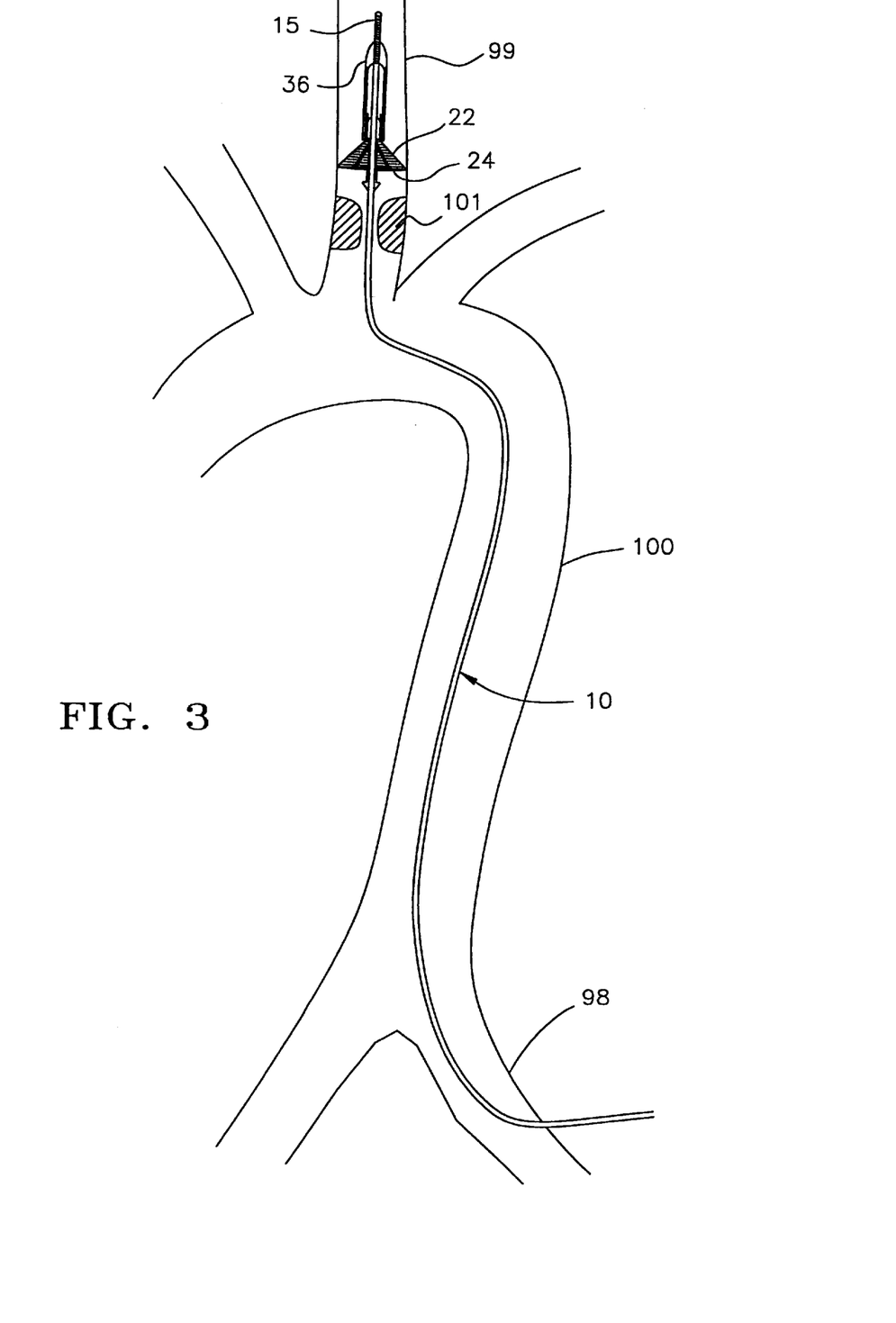
FIG. 3 depicts the catheter filter device of FIG. 1A deployed in the left common carotid artery.

In using the catheter of FIG. 1A for treating atheromatous lesion 101 in left common carotid artery 99 as depicted in FIG. 3, the filter is placed in a collapsed condition and inserted through an incision in left femoral artery 98. The filter is advanced into left common carotid artery 99 via descending aorta 100 and positioned downstream of lesion 101. Atraumatic tip 15 prevents injury to the vascular wall and lesion 101, and minimizes dislodgment of emboli as the filter is passed through lesion 101. The filter is then expanded by opening circumferentially adjacent petals 22 until the engaging mechanism, e.g., hooks, engages adjacent petals. In this way, bases 24 of petals 22 make contact with the vessel wall with minimum gap.

Endovascular devices, such as an atherectomy catheter, stent-deployment catheter, angioplasty catheter, electrophysiology catheter, aspirator, pressure monitors, and endovascular imaging devices, can be inserted over catheter 10 and advanced to position within lesion 101 for treatment of carotid stenosis. After luminal patency is re-established, the endovascular device is withdrawn. The filter is contracted, and with the captured embolic material, is stowed within the lumen of sheath 36. In this manner, the controlled uniform closure of the petals minimizes bunching of the filter and dislodgment of captured emboli. In certain embodiments, the capture sheath includes filter pores which allow distal blood flow while containing the captured debris in the petals during stowage.

Figure 4:
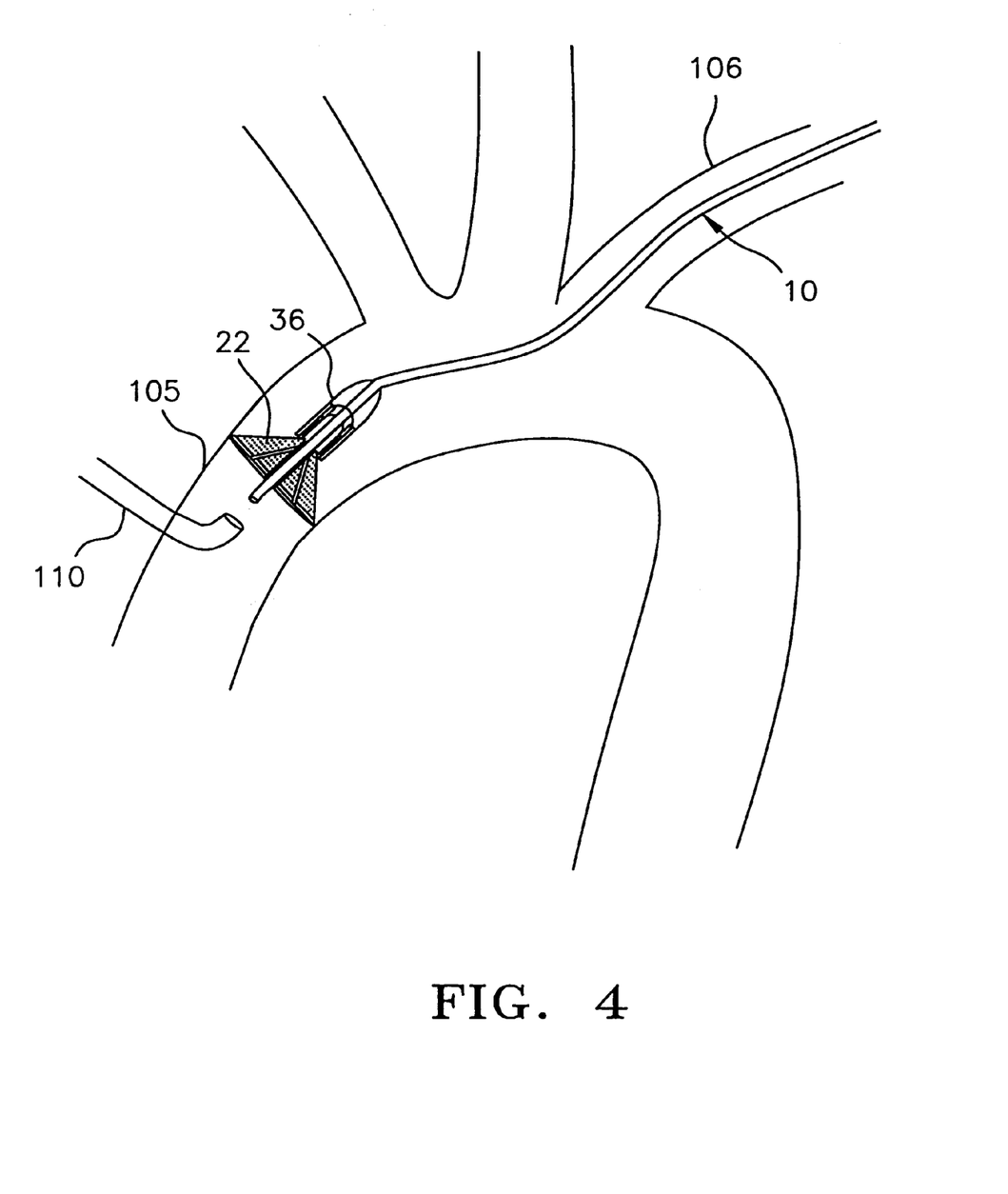
FIG. 4 depicts another embodiment of the filter device deployed in the ascending aorta.

FIG. 4 depicts another embodiment of the filter device inserted in ascending aorta 105 through left subclavian artery 106. The filter is expanded downstream of cannula 110, with the base of the conical filter opening distal to its vertex (relative to the proximal end of the catheter). Capture sheath 36, which comprises a tubular member having a lumen shaped to receive the conical filter when the filter is contracted, is mounted proximal the filter in this case. During cardiopulmonary bypass, for example, aortic cannula 110 is inserted upstream the filter to provide perfusion to peripheral organs. The pores of the filter allow passage of blood but not embolic material, such as thrombi, calcium, myocardial debris, and/or atheromatous plaque. In certain embodiments, each pore will be covered by a mesh filter. In the embodiments of the filter devices that are to be used in the aorta, pore size is 500 μm or less, more preferably 400 μm or less, more preferably 300 μm or less, more preferably 200 μm or less, more preferably 100 μm or less, more preferably 50 μm or less and usually larger than at least a red blood cell. Typical dimensions include pore size of 20–500 μm, and a petal thickness of 0.0005–0.003 inches.

Figure 5A:
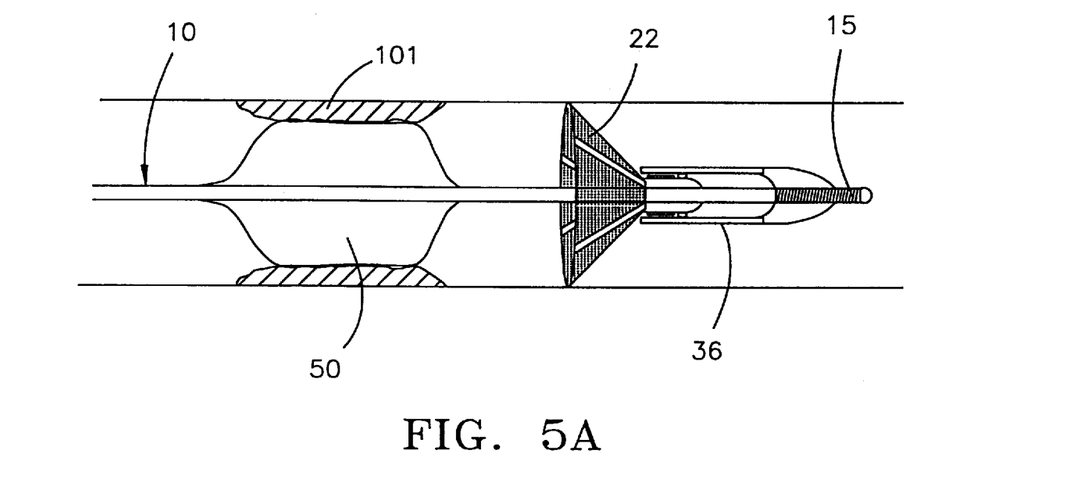
FIG. 5A depicts another embodiment of the catheter filter device having an angioplasty balloon mounted on a distal region.

Percutaneous translumenal angioplasty has been successful in treating arterial stenoses as well as occlusive venous thrombosis resistant to thrombolysis. See American Heart Journal, 125 (2 Pt 1): 362–6 (1993), incorporated herein by reference in its entirety. FIG. 5A depicts another embodiment of the catheter filter device having angioplasty balloon 50 mounted on the distal region of catheter 10 proximal the filter. With the angioplasty balloon in a deflated state and the filter in a contracted state, catheter 10 is inserted percutaneously to position balloon 50 adjacent plaque 101. The filter is expanded, and then the atheromatous plaque is compressed by inflating balloon 50 while the filter is expanded, thereby dilating the stenosis in the vessel and preventing distal embolization. In certain embodiments, a stent is closely associated with the angioplasty balloon. The stent is typically crimped onto the balloon and is capable of controlled radial expansion in the region of interest upon application of a radial, outwardly extending force from the interior of the stent. The construction of the catheter system carrying a stent is described in detail in Jang et al., U.S. Pat. No. 5,749,848, which is incorporated herein by reference in its entirety.

Figure 5B:
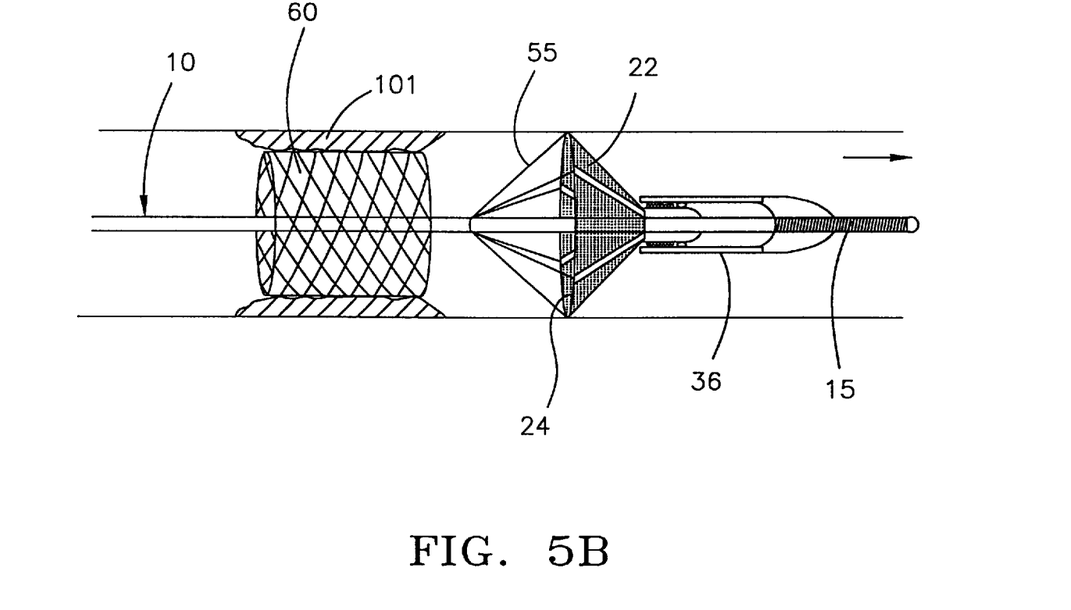
FIG. 5B depicts another embodiment of the catheter filter device having an expandable stent mounted on a distal region.

FIG. 5B depicts another embodiment of the catheter filter system having struts 55 to facilitate stowage of petals 22. The struts are mounted proximal to the filter and are attached to base 24 of each petal. Catheter 10 also includes self-expanding stent 60 mounted proximal to the filter. In use, catheter 10 carrying the collapsed stent and filter is inserted percutaneously and advanced to position the stent within atheromatous lesion 101. The filter is expanded downstream the lesion to capture embolic debris, and then stent 60, made of memory retaining material, e.g., nitinol, expands under body temperature to re-establish luminal patency.

Figure 6:
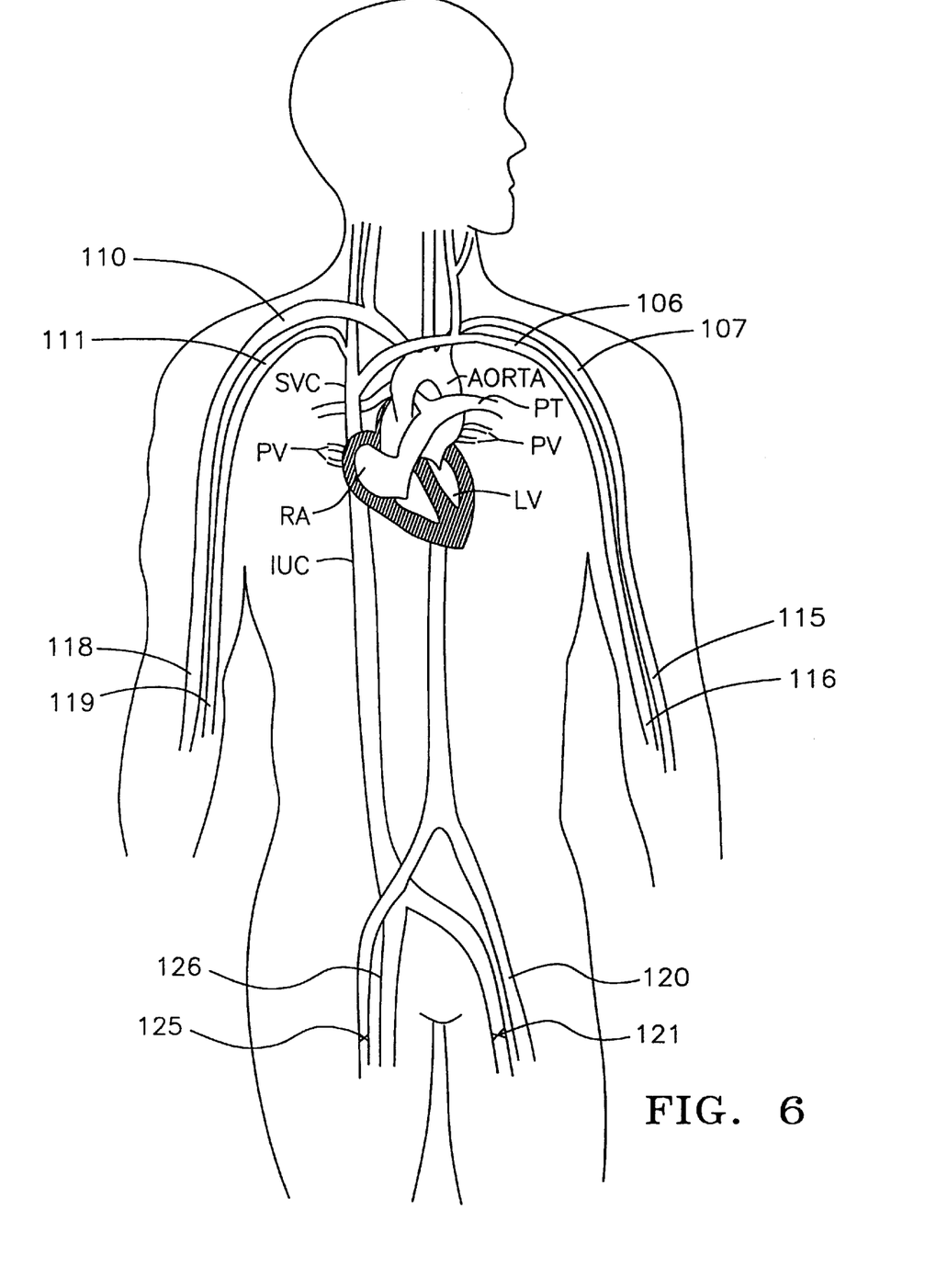
FIG. 6 depicts various percutaneous insertion sites for the filter device of the present invention.

Various percutaneous insertion sites for the catheter filter devices disclosed herein are depicted in FIG. 6. The catheter can be inserted through an incision on right subclavian artery 110, left subclavian artery 106, right brachial artery 118, left brachial artery 115, right femoral artery 125, or left femoral artery 120 to enter a patient's arterial circulation. The catheter can also be inserted through an incision on right subclavian vein 111, left subclavian vein 107, right cubital vein 119, left cubital vein 116, right femoral vein 126, or left femoral vein 121 to enter a patient's venous circulation.

The length of the catheter will generally be between 30 and 300 centimeters, preferably approximately between 50 and 180 centimeters. The inner diameter of the catheter will generally between 0.2 and 0.7 millimeters, preferably approximately between 0.25 and 0.5 millimeters. The filter will be capable of expanding to an outer diameter of at least 0.2 centimeters, more preferably at least 0.5 centimeters, more preferably at least 1.0 centimeters, more preferably at least 1.5 centimeters, more preferably at least 2.0 centimeters, more preferably at least 2.5 centimeters, more preferably at least 3.0 centimeters, more preferably at least 3.5 centimeters, more preferably at least 4.0 centimeters, more preferably at least 4.5 centimeters, more preferably at least 5.0 centimeters. The filter will be capable of contracting to an outer diameter of between 0.05 and 2.0 millimeters, preferably approximately between 0.8 and 1.2 millimeters. The outer diameter of the capture sheath will generally be between 1.2 and 2.2 millimeters, preferably approximately between 0.4 and 1.9 millimeters. These ranges cover suitable diameters for both pediatric and adult use. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. Moreover, it will be understood that each and every feature described for any given embodiment or in any reference incorporated herein, can be combined with any of the other embodiments described herein.

What is claimed is:

1. A blood filter device, comprising:
   a catheter having proximal and distal ends; and
   an expandable filter mounted at the distal end of the catheter, the filter comprising a plurality of circumferentially adjacent porous segments, each segment shaped generally as an equilateral triangle bounded by first and second sides and a base, each of the first and second sides having a hook that engages the circumferentially adjacent segments,
   wherein the segments are arranged about the surface of a cone having an expandable open base, wherein the filter opens by expanding the open base until the hooks engage adjacent segments, preventing further expansion.

2. The device of claim 1, wherein the filter comprises three porous segments.

3. The device of claim 1, wherein each porous segment comprises a material having laser cut pores.

4. The device of claim 3, wherein said each porous segment comprises a plastic material.

5. The device of claim 4, wherein the plastic material is selected from the groups consisting of polyester and polyvinylidene fluoride.

6. The device of claim 1, wherein each side and the base of each segment is linear.

7. The device of claim 1, wherein the hook comprises a fold along the edge of each of the first and second sides.

8. The device of claim 1, wherein the base of the cone opens proximal a vertex of the cone.

9. The device of claim 8, wherein the catheter extends distally beyond the vertex of the cone.

10. The device of claim 9, further comprising a distal capture sheath comprising a tubular member having a lumen shaped to receive the filter when the filter is contracted.

11. The device of claim 9, further comprising a proximal capture sheath comprising a tubular member having a lumen shaped to receive the conical filter when the filter is contracted.

12. The device of claim 1, wherein each segment further comprises an extension bonded to the vertex of the triangle and extending away from the base.

13. The device of claim 12, wherein each extension is bonded to the catheter.

14. The device of claim 1, wherein the catheter further comprises an atraumatic tip at the distal end.

15. The device of claim 1, wherein the base of the cone opens distal a vertex of the cone.

16. The device of claim 1, wherein the catheter further comprises an angioplasty balloon.

17. The device of claim 1, wherein the catheter further comprises a stent.

18. The device of claim 1, wherein the base of each segment is curved, and wherein each segment has the shape of a sector bounded by first and second radii and the included arc of a circle.

19. The device of claim 18, wherein the sector includes an arc of 10–120°.

20. A blood filter device, comprising:

a catheter having a proximal and distal ends; and an expandable filter mounted at the distal end of the catheter, the filter comprising a plurality of circumferentially adjacent porous segments, each segment shaped generally as an equilateral triangle bounded by first and second sides and a base, each of the first and second sides having means for engaging the circumferentially adjacent segments, wherein the segments are arranged about the surface of a cone having an expandable open base, wherein the filter opens by expanding the open base until the means for engaging adjacent segments engage adjacent segments, preventing further expansion.

* * * * *